United States Patent [19]
O'Donnell, Jr.

[11] Patent Number: 5,921,245
[45] Date of Patent: Jul. 13, 1999

[54] METHOD FOR MODIFICATION OF ANTI-SOCIAL BEHAVIOR

[76] Inventor: Francis E. O'Donnell, Jr., 709 The Hamptons La., Town & Country, Mo. 63017

[21] Appl. No.: 08/866,802

[22] Filed: May 30, 1997

Related U.S. Application Data

[XX .
[60] Provisional application No. 60/019,127, Jun. 3, 1996.
[51] Int. Cl.⁶ .................................................. A61B 19/00
[52] U.S. Cl. ........................................... 128/898; 600/407
[58] Field of Search ................................... 128/898, 897; 600/407, 411, 427

[56] References Cited

U.S. PATENT DOCUMENTS

| | | | |
|---|---|---|---|
| 5,617,855 | 4/1997 | Waletzky et al. | 600/586 |
| 5,787,886 | 8/1998 | Kelly et al. | 600/407 |

*Primary Examiner*—Mickey Yu
*Assistant Examiner*—Kelly O'Hara
*Attorney, Agent, or Firm*—Paul M. Denk

[57] ABSTRACT

Precise, three-dimensional localization of neuroanatomic substrates responsible for an established pattern of anti-social behavior such as violence, substance abuse, pedophilia and the like is used to guide temporally and spatially coordinated pulsed multi-origin ablative modalities, wherein the pulse duration is shorter than thermal relaxation time of the target tissue. By selectively destroying aberrant neural networks, the anti-social behavior is eliminated while minimizing unwanted neurologic side-effects.

14 Claims, 1 Drawing Sheet

METHOD FOR MODIFICATION OF ANTI-SOCIAL BEHAVIOR

This application claims benefit of provisional application Ser. No. 60/019,127, filed Jun. 3, 1996.

BACKGROUND OF THE INVENTION

It is well-established that rehabilitation programs for most anti-social behavior is inadequate. The very high rate of recidivism for violent criminals, drug abusers, and pedophiles, for example, is well-established. Simply building more prisons to warehouse these individuals has placed a severe burden upon the economic resources of society. Moreover, the personal tragedy of a life wasted by fatal behavior flaws defies economic analysis.

Our understanding of the origins of aberrant behavior has increased dramatically in the last decades. The ability to successfully control the extremes of aberrant behavior such as schizophrenia by neuro-pharmacologic manipulation suggested that a neurotransmitter-related abnormality could be the source of less extreme abnormal behavior. The more recent success of psychoactive drugs such as Prozac on personality traits such as shyness confirmed this concept.

In addition, neuropharmacologic research has identified specific neuroanatomic sites involved in specific anti-social behavior. For example, Snyder's discovery of endorphins and their localization has pinpointed a critical site involved in narcotics abuse.

As neurophysiologists have explored the neuroanatomic substrate for learned behavior it has become apparent that interneuronal connectivity is influenced by repetitive stimuli (behavior) and that, once established, this neuroanatomic configuration could perpetuate unwanted, anti-social behavior.

Pharmacologic manipulation of unwanted behavior patterns is limited by the multi-functionality of many neurotransmitters. That is to say, for example, the lack of the neurotransmitter seratonin in the limbic system is associated with aggression (violence), but it is also involved in the production of melatonin which regulates diurnal rhythm in the pineal gland. Moreover, to be effective, pharmacologic therapy requires voluntary compliance.

SUMMARY OF THE INVENTION

The present invention describes an apparatus and method for permanent elimination of anti-social behavior by identifying, precisely locating, and selectively ablating the neural networks that are responsible for the undesirable activity.

The present invention consists of a stereotactic helmet which is used to provide precise three-dimensional localization in space of the intracranial contents. The helmet is fabricated from non-metallic materials. It contains a matrix or the like on its surface for subsequent placement of ablative modalities. The helmet is worn by the subject during neuroanatomic mapping. Nuclear magnetic resonance (NMR) scanning with or without neurotransmitter markers can be used. As an adjunct, or alternatively, a positive emission tomography (PET) scan can be used to map the area responsible for the abnormal behavior. In addition, stereotactically-guided electrophysiologic recording by fine intra-cerebral electrode placement can be performed to further refine localization. In another preferred embodiment, the magnetic-encephalography is used to identify the target site. Regardless of exact imaging modality, the target site is activated by the subject during the mapping process. "Activation" may be facilitated by the arousal of the anti-social impulses through the use of audio or audiovisual presentations that feature known stimuli that elicit the unwanted behavior in the subject.

The three-dimensional data so-generated is used to guide the ablative modalities to precisely eliminate the abnormal neural network. Pulsed deep-penetrating subatomic particles, electromagnetic radiation, or pulsed infrared photons can be used to eliminate the abnormal tissue. Regardless of energy source, the use of a multi-element array applied externally in positions identified by the helmet matrix provide the mechanism required to reach supra-threshold levels for destruction at the target tissue while sparring overlying and surrounding tissue. A convergent array focuses the incident energy into a small submillimeter spot wherein the pulsed energy is temporarily and spatially coordinated to reach a supra-threshold ablation at the focal point in abnormal tissue. By using a pulse duration shorter than the thermal relaxation time of the neural target tissue collateral thermal damage can be minimized. Moreover, by selecting an interval between supra-threshold pulses that is longer than the thermal relaxation time of the target tissue, the risk of collateral thermal damage is reduced.

For example, in one embodiment, pulsed gamma radiation is used to ablate the target tissue. In another embodiment, pulsed neutrons or photons are used to ablate the target. In a third embodiment, infrared photons from a pulsed Nd:YAG laser are used. Alternatively, the sensing microelectrodes can be used to provide a pulsed destructive electric current or local delivery of neurotoxin.

One of the objects of this invention is the elimination of antic-social behavior by selective ablation of responsible neuroanatomic substrate.

A further object of this invention is to provide a method wherein the abnormal tissue is identified by nuclear magnetic resonance scanning.

Yet another object of this invention is to provide a method wherein the abnormal tissue is localized by positive emission tomography.

A further object of this invention is to provide a method wherein the abnormal tissue is localized by micro-electrode electrophysiologic recording.

Another object of this invention is to provide a method wherein a non-metallic helmet provides a reference map for placement of an array of ablative mechanism.

Yet another object of this invention is to provide an ablative mechanism that is short-pulsed.

Still another object of this invention is to provide a method wherein the pulsed ablative mechanism is delivered in a temporarily coordinated fashion.

Another object of this invention is to provide a method wherein the ablative mechanism consists of multiple elements so arranged as to converge on the target tissue.

Still another object of this invention is to provide a method wherein the ablative mechanism is deep penetrating.

Another object of this invention is to provide a method wherein a microelectrode is used to cause destruction of the identified abnormal tissue by electric current or chemical means.

Yet another object of this invention is to provide a method wherein the ablative mechanism is short-pulsed so that the pulse duration is shorter than the thermal relaxation time of the target tissue.

Still another object of this invention is to provide a method wherein the ablative mechanism is pulsed subatomic particles such as protons or neutrons.

Yet another object of this invention is to provide a method wherein the ablative mechanism is a pulsed electromagnetic radiation such as gamma radiation.

A further object of this invention is to provide a method wherein the ablative mechanism is an infrared laser such as a pulsed Nd:YAG laser.

Another object of this invention is to provide a targeting of and the interruption to the neuronal pathway from the orbital cortex-cingulate cortex-candate nucleus.

Still another object of this invention is to provide means for ablation of the morphine receptors in the hypothalamus in order to control narcotics abuse.

Still another object of this invention is to provide means for ablating the dopamine receptors in the hypothalamus to control pleasurable activity caused by aberrant behavior.

Yet another object of this invention is to provide means for ablating that portion of the limbic system that is responsible for sexual arousal in response to inappropriate stimuli.

Still another object of this invention is to provide means for ablating that portion of the hypothalamus characterized by seratonin receptors in order to control aggression.

Yet another object of this invention is to provide a method wherein the target site for treatment is identified by nuclear magnetic resonance scanning.

Still another object of this invention is to provide a method wherein the target site is localized by positive emission tomography.

Yet another object of this invention is to provide a method wherein the target is localized by micro-electrode electrophysiologic recording.

Still another object of this invention is to provide a method whereby the target site is localized by magnetoencephalography.

Yet another object of this invention is to provide a non-metallic helmet that provides a reference map for placement of an array of an ablative mechanism.

Still another object of this invention is to provide an ablative mechanism which consists of multiple elements so arranged as to converge on the target site.

Still another object of this invention is to provide an ablative mechanism which is short pulsed with an integral between pulses that is longer than the thermal relaxation time of the target tissue.

DESCRIPTION OF THE PREFERRED EMBODIMENT

Figure 1:
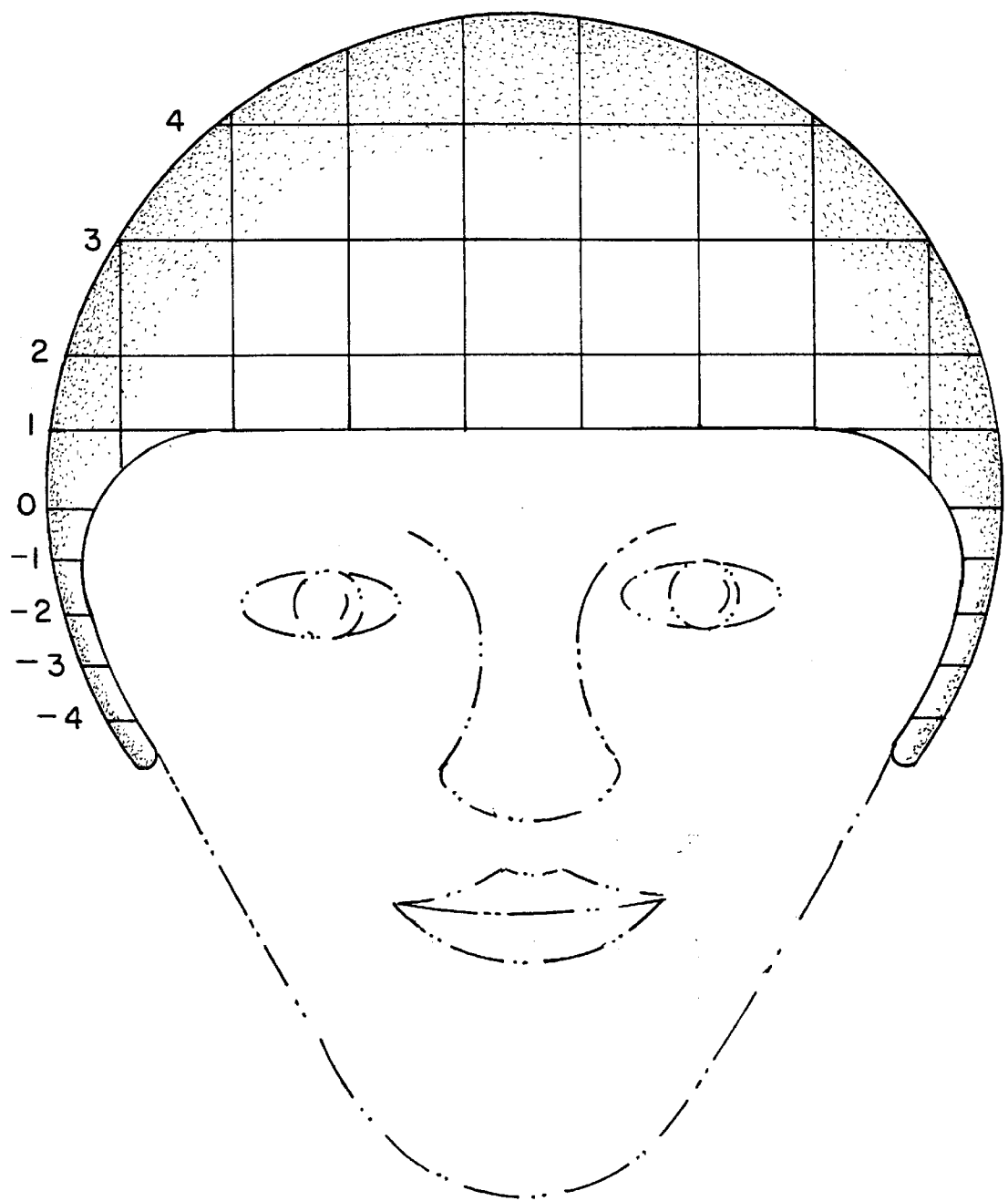
FIG. 1 is an isometric view of the helmet means worn by the subject during neuronanatomic mapping utilizing magnetic resonance or tomographic scanning.

FIG. 1 discloses the type of helmet utilized for stereotactic analysis of the patient's head, wherein application of the helmet can be used to provide nuclear magnetic resonance scanning of the head, or provide positive emission tomographic scanning, or through the use of stereotactical-guided electrophysiological recording by fine intracerebral electrodes, for the purpose of furnishing a precise three-dimensional localization in space of the intracranial contents of the head. The three-dimensional data so obtained is then used to guide the electrode means precisely for generation of the pulsed deep-penetrating subatomic particles, electromagnetic radiation, or pulsed infrared photons, for eliminating that abnormal tissue location previously detected and determined as the source of abnormal behavior, and which requires treatment. Regardless of the energy source applied, the use of the multi-element array that is applied externally in positions identified by the helmet matrix provides the mechanism required to reach the supra-threshold levels for destruction at the target tissue, while sparing any overlying or ambient tissue, from any exposure or treatment at all. The convergent array of pulsed particles focus the incident energy into a very small microspot, wherein the pulsed energy is temporarily and spatially coordinated to reach a supra-threshold ablation level, at the focal point of the abnormal tissue. By using a pulse duration shorter than the thermal relaxation time of the neurotarget tissue, collateral thermal damage can be minimized. Obviously, in the radiation process, it is just as likely that laser means may be applied to furnish the infrared photons needed to generate the sufficient ablation or pulsed deep-penetrating subanatomic particles to attain the elimination of the detected site of abnormal tissue.

In a preferred embodiment, pathway that originates from the orbital portion of the frontal cortex to the cingulate cortex and which terminates in the head of the candate nucleus is known to be a common pathway for obsessive-compulsive disorders and for so-called Tourette's syndrome of motor tics and verbal repetitions. In prior art, neurosurgical interruption of this pathway by severing it with a cutting instrument has effectively relieved the undesirable behavior, but the risks and side effects of this invasive approach were generally unacceptable. The present invention can be used to non-invasively identifying and ablate (interrupt) this pathway. It is suspected that this pathway may be a common pathway for a wide variety of abnormal behavior patterns such as rage reactions (explosive violence) and sexual perversions such as pedophilia.

In another embodiment, the morphine receptors in the hypothalamus are identified by NMR after administration of morphine analogues tagged for NMR imaging. The portion of the hypothalamus containing the receptors is ablated by delivery of pulsed gamma radiation.

In another embodiment, the dopamine receptors in the hypothalamus responsible for pleasurable activity due to undesirable activity such as smoking, are identified by administering nicotine tagged with a ligand for NMR imaging, The nicotine receptors responsible for dopamine release are targeted for ablation using pulsed gamma radiation.

In another embodiment, magnetoencephalography is used to identify sites in the limbic system activated by pornographic stimuli in order to guide selective ablation in pedophilia.

In another embodiment the portion of the hypothalamus responsible for seratonin-mediated aggression is identified by administering seratonin tagged for NMR imaging in conjunction with stimuli selected to provoke a violent reaction.

The matrix system as shown in the FIGURE incorporates intersecting coordinates identified by number, as on the coronal section, and alphabetical letters, as on the sagittal section, and the construction is used to help identify the surface topography in relationship to the subsurface neuro anatomic targets during performing of the treatment. This matrix-cranial marker, or helmet, is also used to help placement and angular orientation of the externally pulsed modalities for delivery of therapeutic energy to the target situs.

I claim:

1. A method for modification of unwanted behavior, the method including:

identifying neuronal pathways in the brain of a patient responsible for the unwanted behavior;

targeting a portion of the neuronal pathway; and non-invasively disrupting the neuronal pathway to eliminate the unwanted behavior.

2. The method of claim 1 wherein the step of identifying the pathway includes activating the neuronal pathway and scanning the patient's brain to provide a precise three-dimensional localization in space of the brain.

3. The method of claim 2 wherein the step of scanning the brain includes conducting at least one of a nuclear magnetic resonance (NMR) scan, a positive emission tomographic (PET) scan, and a stereotactical-guided electrophysiological recording using fine intracerebral electrodes.

4. The method of claim 2 wherein the step of identifying the neuronal pathway includes;

administering morphine analogues tagged for NMR imaging to identify morphine receptors in the hypothalamus; and the step of non-invasively disrupting the pathway includes ablating tissue by delivery of pulsed gamma radiation.

5. The method of claim 2 wherein the step of identifying the neuronal pathway includes;

administering nicotine tagged with a ligand for NMR imaging to identify dopamine receptors in the hypothalmus; and the step of non-invasively disrupting the neuronal pathway including ablating tissue by delivery of pulsed gamma radiation.

6. The method of claim 2 wherein the step of identifying the neuronal pathway includes stimulating the undesirable neuronal pathway in the limbic system of the patient's brain by exposing the patient to selected stimuli and identifying the stimulated neuronal pathway by magnetoencephalography.

7. The method of claim 2 wherein the step of identifying the neuronal pathway includes administering seratonin tagged for NMR imaging in conjunction and exposing the patient to stimuli selected to provoke a violent reaction to identify the hypothalmus responsible for seratonin-mediated aggression.

8. The method of claim 2 wherein the step of targeting the portion of the neuronal pathway includes placing a helmet on the patient's head, wherein the helmet has an outer surface with coordinate identifying indicia provided thereon, the coordinate identifying indicia including intersecting coronal lines and sagittal lines which cooperate to create a coordinate system.

9. The method of claim 8 wherein the step of disrupting the neuronal pathway includes non-invasively ablating tissue in the neuronal pathway.

10. The method of claim 9 wherein the step of ablating the tissue in the neuronal pathway includes precisely guiding energy to the targeted area.

11. The method of claim 10 wherein the energy includes at least one of pulsed deep-penetrating subatomic particles, electromagnetic radiation, and pulsed infrared photons to the targeted area.

12. The method of claim 10, further including the steps of:

positioning energy generators in a multi-element array wherein the energy is applied externally in positions identified by the helmet matrix;

activating the energy generators to produce energy streams which converge at the targeted area; and reaching a supra-threshold energy level for destroying the target tissue without damaging the overlying or ambient tissue from exposure to the converging energy streams.

13. The method of claim 12 wherein the pulsed energy is temporally and spatially coordinated to reach a supra-threshold ablation level, at the focal point of the abnormal tissue.

14. The method of claim 13 wherein the generated energy includes generating energy streams in pulsed durations shorter than the thermal relaxation time of the neurotarget tissue.

\* \* \* \* \*